United States Patent
Borm et al.

(10) Patent No.: US 10,835,698 B2
(45) Date of Patent: Nov. 17, 2020

(54) APPARATUS FOR RESPIRATING OF PATIENTS

(75) Inventors: Pieter Borm, Eindhoven (NL); Bart Westerkamp, Alkmaar (NL)

(73) Assignee: LÖWENSTEIN MEDICAL TECHNOLOGY S.A., Luxembourg (LU)

( * ) Notice: Subject to any disclaimer, the term of this patent is extended or adjusted under 35 U.S.C. 154(b) by 0 days.

(21) Appl. No.: 13/500,227

(22) PCT Filed: Oct. 6, 2010

(86) PCT No.: PCT/NL2010/000143
§ 371 (c)(1),
(2), (4) Date: Jun. 21, 2012

(87) PCT Pub. No.: WO2011/043651
PCT Pub. Date: Apr. 14, 2011

(65) Prior Publication Data
US 2012/0255547 A1    Oct. 11, 2012

(30) Foreign Application Priority Data
Oct. 7, 2009 (NL) .................................... 1037373

(51) Int. Cl.
*A61M 16/01* (2006.01)
*A61M 16/22* (2006.01)

(52) U.S. Cl.
CPC ............. *A61M 16/01* (2013.01); *A61M 16/22* (2013.01); *A61M 2230/432* (2013.01)

(58) Field of Classification Search
CPC .......... A61M 16/0003; A61M 16/0045; A61M 16/0057; A61M 16/06; A61M 16/0063;
(Continued)

(56) References Cited

U.S. PATENT DOCUMENTS 3,556,095 A * 1/1971 Ismach .................... 128/204.28
3,612,048 A * 10/1971 Takaoka .................. 128/204.25
(Continued)

FOREIGN PATENT DOCUMENTS

| GB | 2338902 A | 1/2000 |
| WO | 2007033271 A1 | 3/2007 |

OTHER PUBLICATIONS

International Search Report for corresponding International Application No. PCT/NL2010/000143.

*Primary Examiner* — Rachel T Sippel
(74) *Attorney, Agent, or Firm* — Egbert, McDaniel & Swartz, PLLC

(57) ABSTRACT

An apparatus for respirating a patient has a gas circulation device for circulating a gas in one direction in a line system, a pressure varying device suitable for varying a pressure of the gas in the line system in accordance with the desired respirating the pattern, a measurement sensor cooperative with the gas in the line system so as to measure a flow rate and composition of the gas, an absorber device suitable for withdrawing carbon dioxide as exhaled by the patient, a bypass line having a closing device suitable for completely or partially leading the respiratory gas outside of the line system, and a circulation blower cooperative with the line system so as to provide a continuous flow of gas in one direction through the line system.

18 Claims, 2 Drawing Sheets

(58) Field of Classification Search
CPC ......... A61M 16/0066; A61M 16/0069; A61M 16/0075; A61M 16/01; A61M 16/22
USPC ............ 128/203.12–15, 203.25, 204.18–19, 128/204.21–22, 205.12, 205.27, 205.28
See application file for complete search history.

(56) References Cited

U.S. PATENT DOCUMENTS

| | | | | |
|---|---|---|---|---|
| 5,398,675 | A | * | 3/1995 | Henkin et al. ............ 128/203.12 |
| 6,591,836 | B1 | * | 7/2003 | Fuhrman et al. ......... 128/205.24 |
| 2004/0216743 | A1 | | 11/2004 | Orr et al. |
| 2006/0196505 | A1 | * | 9/2006 | Izuchukwu .............. 128/203.15 |
| 2009/0056713 | A1 | * | 3/2009 | Cortez et al. ............ 128/203.26 |
| 2010/0147302 | A1 | * | 6/2010 | Selvarajan ............. A61M 16/00 128/204.23 |
| 2012/0247467 | A1 | * | 10/2012 | Borm et al. .............. 128/203.25 |
| 2015/0083121 | A1 | * | 3/2015 | Fisher ................. A61M 16/024 128/202.22 |

* cited by examiner

APPARATUS FOR RESPIRATING OF PATIENTS

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The present invention relates to an apparatus for the respirating of patients, for anesthesia through inhalation and for the administering of therapeutic gases through inhalation, which apparatus is provided with means for the circulating in one direction in a line system of breathing gas, an anesthetic gas or a therapeutic gas, with means for varying the pressure in the line system in accordance with a certain respirating pattern, with means for measuring the flow of the gas and the composition of the gas, whilst the line system is provided with connecting means for the patient and with further supplies for the various components of the respiratory gas and with a line system part in which an absorber device is provided for the withdrawing of the carbon dioxide exhaled by the patient in the line system.

2. Description of Related Art Including Information Disclosed Under 37 CFR 1.97 and 37 CFR 1.98

For medical considerations it may be desirable to maintain or alter a certain amount of carbon dioxide in the respiratory gas, so that it can get more near the desired bodily values. This can be attained by changing the ventilation or rather the respiration. This however influences for instance the intake or release of oxygen or another gas. This may be undesirable. It is further known to enrich the inhalation gas with carbon dioxide. Also are known apparatuses, in which the line system is provided with a by-pass line with closing means by means of which the respiratory gas completely or partly can be led outside of the line system part in which the absorber device is provided, and whereby, in this manner, the absorber device can completely or partly be switched out, so that no or less removal of the carbon dioxide exhaled by the patient takes place. The patient then breathes in again the gas that is led through the by-pass line (rebreathing).

Like this the U.S. Pat. No. 6,131,571 describes an apparatus in which in the line system a by-pass line is provided by means of which the respiratory gas can be led outside of the line system part containing the absorber device. This publication describes that in the case in which it is intended to quickly wash away vaporous anesthetica out of the line system, the by-pass line is opened to lead the respiratory gas outside the absorber device. This makes it possible to ventilate the patient quickly without the concentration of $CO_2$ in the body decreasing too much.

This known apparatus does not comprise means by which the opening and closing of the by-pass line can be controlled in dependence on a measurement in the line system of the concentration of $CO_2$ in the respiratory gas.

The International application WO-A-9636385 describes an apparatus in which a device for analysing gas is provided, on the basis of which personnel can operate a valve in a by-pass line by means of which the respiratory gas completely or partly can be led outside of the line system part in which the absorber device is provided.

The International application WOA-9940961 describes an apparatus in which in a line system a by-pass line is provided by means of which respiratory gas completely or partly can be led outside of the line system part in which the absorber device is provided, while the completely or partly opening and closing of the by-pass line is controlled by a control unit in dependence on a measurement of the concentration of $CO_2$ in the respiratory gas in the line system. With this known apparatus it is aimed for to maintain the concentration of $CO_2$ in the blood at a particular level, in order to prevent a long lapse of time between the end of the anesthesia and the beginning of the spontaneous breathing.

This known apparatus has the drawback, that the adapting of the concentration of $CO_2$ in the gas to the desired level comes about rather slowly relative to the changes in the body, that is to say, takes longer than 5 minutes, while a change in the body of the patient can take place within 2 minutes. Because of this it is not possible to realize a quick and accurate control of the amount of $CO_2$ in the respiratory gas at the end of a respiratory movement of the patient (endtidal $CO_2$), which is of great importance in case of for instance operations on the brain. In case of operations on the brain it is desired that the $PCO_2$ in the brain remains constant. The $PCO_2$ in the brain is directly related to the $PCO_2$ in the blood and this in turn is related to the end-tidal concentration of $CO_2$.

Also it is desirable during these operate interventions to maintain the supply of oxygen to the body optimum. Hyperventilation may be desirable. However one then has to apply rebreathing to keep the end-tidal concentration of $CO_2$ at level. The problem is, that a change in the end-tidal concentration of $CO_2$ can occur quickly (within a few minutes). In the present rebreathing systems the time of response is very long, from many minutes to over 30 minutes. Because of this the known method of control is not suitable for optimum clinical use.

The invention aims to obviate this drawback of the known apparatus and to provide an apparatus, by means of which a more accurate control of the amount of carbon dioxide in the respiratory gas can take place.

BRIEF SUMMARY OF THE INVENTION

The apparatus according to the invention to that end is characterized, in that a control unit is provided by means of which the operating of the closing means takes place in dependence on one or more measurements of the concentration of carbon dioxide in the respiratory gas in the line system, and wherein the line system is provided with a circulation blower.

According to a characteristic of the apparatus according to the invention the circulation blower has a capacity between 15 and 120 litre per minute.

According to a further characteristic of the apparatus according to the invention the circulation blower has a capacity between 30 to 60 litre per minute.

According to a further characteristic of the apparatus according to the invention the capacity of the circulation blower is adapted to the volume of the line system, in such a way, that the duration of one circulation of the gas is 10 seconds at the most, more in particular 5 seconds at the most, more in particular 3 seconds at the most.

According to a further characteristic of the apparatus according to the invention the duration of one circulation is 2.5 seconds at the most.

With the apparatus according to the invention it is possible to accurately maintain the concentration of carbon dioxide in the body of the patient at the desired level. More in particular it is possible to ascertain immediately a physiological change in the patient that is occurring all of a sudden, to determine the ratio between the flow through the absorber device and the flow outside of the absorber device and to bring the concentration of carbon dioxide at the desired level by a quick mixing by means of the circulation blower.

According to yet a further characteristic of the apparatus according to the invention in at least two places in the line system means are provided for the measuring of the concentration of $CO_2$ in the gas.

According to another characteristic of the apparatus according to the invention one of the means for the measuring of the concentration of $CO_2$ in the gas is provided near the connection to the patient, more in particular at the mouth of the patient.

According to a further characteristic of the apparatus according to the invention one of the means for the measuring of the concentration of $CO_2$ in the gas is provided in a part of the line system outside the connection to the patient.

According to a further characteristic of the apparatus according to the invention one of the means for the measuring of the concentration of $CO_2$ in the gas is provided in a part of the line system which, as seen downstream, is positioned behind the means for the varying of the pressure in the line system.

Further characteristics and features of the invention will be described with reference to the drawing of an example of an embodiment.

DETAILED DESCRIPTION OF THE INVENTION

Figure 1:
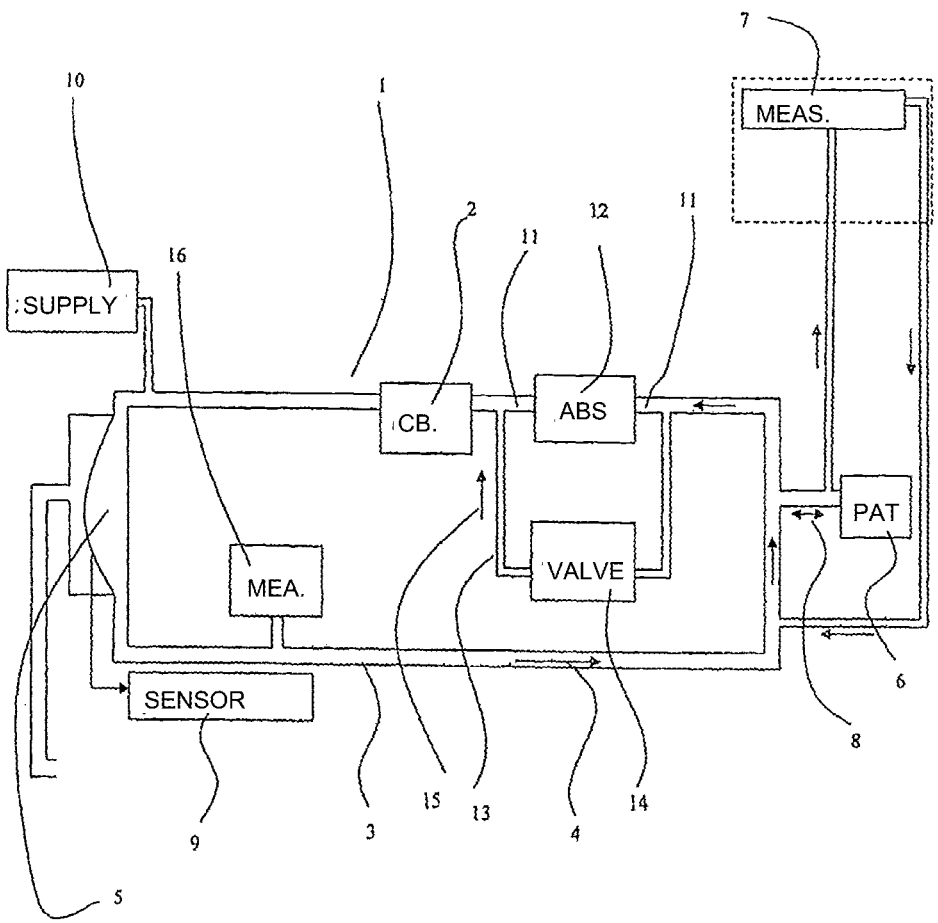
FIG. 1 schematically shows an example of an embodiment of the apparatus according to the invention.

As is shown in FIG. 1, the apparatus 1 is provided with means, such as a circulation blower 2, for the circulating in one direction 4 in a line system 3 of respiratory gas, and of means 5, for instance a membrane or bellows, for varying the pressure in the line system 3 in accordance with a certain respirating pattern to make possible the respiration of the patient 6.

Further means are provided, such as an apparatus 7, for determining the composition of the gas inhaled and the gas exhaled 8 by the patient. In the drawing is shown the principle of sampling removal. If so desired the gas that has been removed can be fed back into the system. It is also possible to make use of a measuring system directly in the gas inhaled and the gas exhaled 8. In the closed system by means of the sensor 9 the volume or the flow of the respiration by the patient can be measured, during spontaneous respiration as well as during breathing upon the patient or in a given case supportive breathing upon the patient. The apparatus 10 provides the supply of the gases and the vaporous anesthetica into the system.

In the example of the embodiment shown, in the line system 3, as seen in the direction of circulation 4 of the respiratory gas, in front of the circulation blower 2 a line system part 11 is provided, in which is comprised the absorber device 12 for the withdrawing of the carbon dioxide exhaled by the patient in the line system.

To the line system 3 further a by-pass line 13, extending parallel to the line system part 11, is connected, by means of which the respiratory gas can be led completely or partly outside the line system part 11 containing the absorber device 12. In the by-pass line 13 a regulating device 14 is provided, for instance a regulating valve, by means of which the ratio between the volume of the flow 15 of respiratory gas through the by-pass line 13 and that through the absorber device 12 can be adjusted. By means of this the extent to which the patient breathes in gas that has been purified from carbon dioxide can be adjusted, and as a consequence thereof the amount of carbon dioxide in the body can be adjusted.

In the example of the embodiment shown at at least two places in the line system measuring devices are provided for the measuring of the concentration of $CO_2$ in the gas, whereby one measuring device 7 is provided near the mouth of the patient 6 and a second measuring device 16 is provided in the part of the line system which, as seen in the direction 4 of the gas flow, is positioned behind the membrane or bellows.

By means of a control unit the operating of the regulating valve 14 takes place in dependence on the measurements of the concentration of carbon dioxide in the respiratory gas at the mouth of the patient by the measuring device 7 and further on in the line system by the measuring device 16. On the basis of these measurements the regulating valve 14 is operated and by means of that the ratio between the flow 15 of respiratory gas through the bypass line 13 and that through the absorber device 12 is adjusted. By means of this the extent to which the patient breathes in gas that has not been purified from carbon dioxide is adjusted, and as a consequence thereof the amount of carbon dioxide in the respiratory gas at the end of a respiratory movement of the patient.

The determination of the end tidal concentration of $CO_2$ through the respiration is dependant on the blood circulation. In adults the duration of one circulation of the blood is about 8 seconds; in infants about 3 seconds. The control system has to be quicker than the human, whereby a given is that for a significant change of the concentration of $CO_2$ in the gas the length of time taken up by one circulation of the gas in the line system shall not be more than a third of the length of time involved with one circulation of the blood in the patient. Thus, a system for only adults has to remain below 24 seconds; for infants below 3 seconds.

A guiding principle is that one circulation of the gas in the line system does not take more than three seconds, preferably 2.5 seconds.

In this example of an embodiment the volume of the line system is 2.5 litre while in the line system a circulation blower is provided having in this example of an embodiment a capacity of 60 litre per minute. This results in a circulation time of: 2.5 litre/60 litre/min=0.042 minutes=2.5 seconds.

Taking 2.5 seconds as a guiding principle, in the case of for instance a volume of the line system of 1.25 litre a circulation blower having a capacity of 30 litre per minute has to be applied, in the case of a volume of the line system of 5 litre a circulation blower having a capacity of 120 litre per minute has to be applied, and in the case of a volume of the line system of 0.625 litre a circulation blower having a capacity of 15 litre per minute has to be applied.

With the application of a circulation blower, the capacity of which is adapted to the volume of the circuit, it is possible to bring about and maintain a sufficient fastness of circulation. With this it is attained that the mixing is quicker than that of the processes in the patient, so that a quick and accurate regulation is possible of the et $CO_2$. This is essential to an adequate control of the et $CO_2$, by which for instance during hyperventilation de et $CO_2$ remains at the desired level, notwithstanding changing processes in the patient. By continuously measuring of the concentration of $CO_2$ by means of the measuring devices 7 and 16 respectively at the mouth and further on in the circuit it is possible to ascertain the correct functioning of this quick regulation.

With the apparatus according to the invention, more in particular the application of a circulation blower for providing a sufficiently fast circulation and the control of the ratio between the volume of the gas flow through the bypass line and that through the absorber device on the basis of measurements at at least two places in the line system, it is possible to adequately control the et $CO_2$ irrespective of the extent of hyperventilation. Thereby the regulating valve with regard to the extent of rebreathing in combination with the measurement of the end-tidal $CO_2$ and the intrinsic fastness of the system as a consequence of the application of a circulation blower, an adjustment which is faster than the changes of the processes in the body is attained.

In an example of an embodiment not shown in the drawing the regulating device as an alternative can also be provided in the line system part 11 in series with the absorber device 12.

Figure 2:
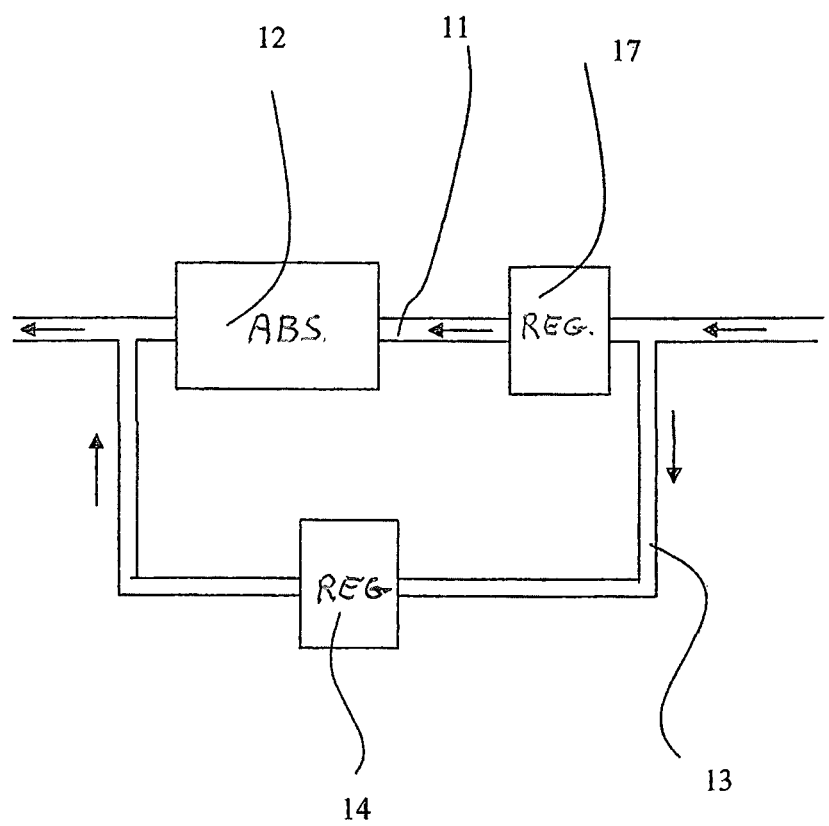
FIG. 2 shows apart of another example of an embodiment of the apparatus according to the invention.

In FIG. 2 an example of an embodiment is shown, in which next to the regulating device 14 in the by-pass line 13 in the line system part 11 a further regulating device 17 is provided.

With the invention an apparatus is provided in which in parallel with the absorber device a by-pass line or rather by-pass is provided with either a regulating device in the flow through the absorber apparatus or a regulating device in the flow through the by-pass, and by means of which the breathing in again of carbon dioxide by the patient (rebreathing of carbon dioxide) can be regulated, by means of which the amount of carbon dioxide in the respiratory gas at the end of a respiratory movement of the patient (et $CO_2$; endtidal $CO_2$) can be regulated at the desired physical level, while the ventilation is allowed to vary.

With the apparatus according to the invention by means of the increased ventilation the gases or in a given case vapours supplied to the patient can be increased to attain a faster wash in of the patient.

Further by means of the increased ventilation the gases or in a given case vapours given off by the patient into the system can be increased in order to obtain attain a quicker wash out of the patient.

We claim:

1. An apparatus for respirating a patient or for administering anesthesia through inhalation by the patient or for administering therapeutic gasses through inhalation by the patient, the apparatus comprising:
    a circulation blower cooperative with a line system so as to circulate gas in only one direction in the line system;
    a pump cooperative with the line system for varying a pressure of the gas in the line system to achieve a desired respirating pattern so as to respirate the patient;
    a plurality of measurement sensors cooperative with the gas in the line system, said plurality of measurement sensors suitable for measuring a flow rate of the gas in the line system and a composition of the gas in the line system, the line system having a connector suitable for connecting to the patient and another connector suitable for connecting to a supply of the gas;
    an absorber device cooperative with the line system, said absorber device suitable for withdrawing carbon dioxide as exhaled by the patient;
    a bypass line connected to the line system, said bypass line having a closing device suitable for completely or partially leading the respiratory gas outside of the line system; and
    a control unit cooperative with said closing device such that said closing device operates depending on one or more measurements of a concentration of carbon dioxide in the respiration gas in said line system.

2. The apparatus of claim 1, said circulation blower circulating the gas at 15 to 120 liters per minute.

3. The apparatus of claim 1, said circulation blower circulating the gas at 30 to 60 liters per minute.

4. The apparatus of claim 1, said circulation blower causing a single gas circulation of a duration of no more than 10 seconds.

5. The apparatus of claim 4, said circulation blower causing a single gas circulation of a duration of no more than 2.5 seconds.

6. The apparatus of claim 1, said line system having a volume of 2.5 liters, said circulation blower circulating the gas at 60 liters per minute.

7. The apparatus of claim 1, said line system having a volume of 1.25 liters, said circulation blower circulating the gas at 30 liters per minute.

8. The apparatus of claim 1, said line system having a volume of 5 liters, said circulation blower circulating the gas at 120 liters per minute.

9. The apparatus of claim 1, said line system having a volume of 0.625 liters, said circulation blower circulating the gas at 15.0 liters per minute.

10. The apparatus of claim 1, further comprising:
    a first carbon dioxide sensor positioned at one location on the line system; and
    a second carbon dioxide sensor positioned at another location on the line system, each of said first and second carbon dioxide sensors suitable for measuring the concentration of the carbon dioxide in the line system.

11. The apparatus of claim 10, said first carbon dioxide sensor positioned adjacent said connector adjacent the patient.

12. The apparatus of claim 11, said second carbon dioxide sensor positioned away from said connector adjacent the patient.

13. The apparatus of claim 10, one of said first and second carbon dioxide sensors positioned downstream of said pressure varying device in said line system.

14. The apparatus of claim 1, said closing device cooperative with the line system and suitable for regulating a ratio between a volume of gas flow through said bypass line and a volume of gas flow through said absorber.

15. The apparatus of claim 14, said closing device positioned on said bypass line.

16. The apparatus of claim 14, said closing device cooperative with said absorber.

17. The apparatus of claim 14, said regulator being a closing device valve.

18. The apparatus of claim 1, said bypass line running parallel to a portion of the line system having said absorber device thereon.

* * * * *